United States Patent
Raines

(10) Patent No.: US 7,560,248 B1
(45) Date of Patent: Jul. 14, 2009

(54) OXIDATION-RESISTANT RIBONUCLEASE INHIBITOR

(75) Inventor: Ronald T. Raines, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/234,028

(22) Filed: Jan. 20, 1999

(51) Int. Cl.
C12N 15/09 (2006.01)
C07K 14/00 (2006.01)

(52) U.S. Cl. .................. 435/69.2; 530/350; 435/199

(58) Field of Classification Search ............... 435/185; 530/350; 536/23.5
See application file for complete search history.

(56) References Cited

U.S. PATENT DOCUMENTS

| 4,966,964 A | 10/1990 | Shapiro et al. | 536/27 |
| 5,019,556 A | 5/1991 | Shapiro et al. | 514/2 |
| 5,266,687 A | 11/1993 | Shapiro et al. | 536/23.1 |
| 5,552,302 A | 9/1996 | Lewis et al. | 435/692 |

FOREIGN PATENT DOCUMENTS

| AU | B-55377/90 | 4/1990 |
| EP | 0 422 217 B1 | 1/1998 |
| WO | WO 98/06845 | 2/1998 |

OTHER PUBLICATIONS

Chen et al., Site specific mutagenesis reveals differences in the structural bases for tight binding of RNase inhibitor to angiogenin and RNase A, Proc. Natl. Acad. Sci USA 94: 1761-1766.*

Hofsteenge, J., "Ribonuclease Inhibitor," *Ribonucleases: Structures and Functions* 19:621-658 (1997).

Kawanomoto, M. et al., "cDNA cloning and sequence of rat ribonuclease inhibitor, and tissue distribution of the mRNA," *Biochimica et Biophysica Acta* 1129:335-338 (1992).

Lee, F. S. et al., "Primary Structure of Human Placental Ribonuclease Inhibitor," *Biochemistry* 27:8545-8553 (1988).

Leland, P. A. et al., "Ribonuclease a variants with potent cytotoxic activity," *Proc. Natl. Aca. Sci. USA* 95:1-7 (1998).

Raines, R. T., "Ribonuclease A," *Chemical Reviews* 98:1045-1065 (1998).

Blazquez, et al., "Oxidation of Sulfhydryl Groups of Ribonuclease Inhibitor in Epithelial Cells is Sufficient for its Intracellular Degradation," *The Journal of Biological Chemistry* 271:18638-18642 (1996).

Byung-Moon, et al., "Variants of ribonuclease inhibitor that resist oxidation," *Protein Science* 8:430-434 (1999).

* cited by examiner

*Primary Examiner*—Richard G Hutson
(74) *Attorney, Agent, or Firm*—Quarles & Brady LLP

(57) ABSTRACT

Mutant forms of ribonuclease inhibitor are described which are rendered more resistant to oxidation while retaining affinity for both ribonuclease and angiogenin. The mutant forms have another amino acid, typically an alanine, substituted for one or more of the adjacent cysteine residues in the wild-type sequence to prevent the formation of unwanted disulfide bonds which can disrupt the effectiveness of the molecule.

11 Claims, 5 Drawing Sheets

```
  1        MSLDIQCEQLSDARWT----ELLPLIQQYQVMRLDDGLTEVRCKDIR
  1        MNLDIHCEQLSDARWT----ELLPLLQQYEVMRLDDGLTEEHCKDIG
  1     MSLDIQSLDIQCEELSDARWA----ELLPLLQQCQVMRLDDGLTEARCKDIS

45    SAIQANPALTELSLRTNELGDAGVGLVLQGLQNPTCKIQKLSLQNCSLTEAGCGVLP
 45    SALRANPSITELCLRTNELGDAGVHLVLQGLQSPTCKIQKLSLQNCSLTEAGCGVLP
 50    SALRVNPALAELNLRSNELGDVGMHCVLQGLQTPSCKIQKLSLQNCCLTGAGCGVLS

102    DVLRSLSTLRELHLNDNPLGDEGLKILCEGLRDPQCRLEKLQLEYCNLTATSCEPLA
102    STLRSLPTLRELHLSDNPLGDAGLRILCEGLLDPQCHLEKLQLEYCRLTAASCEPLA
107    STLRTLPTLQELHLSDNLLGDAGLQLLCEGLLDPQCRLEKLQLEYCSLSAASCEPLA

159    SMLRVKPDFKELVLSNNDFHEAGIHTLCQGLKDSACQLESLKLENCGITSANCKDLC
159    SMLRATRALKELIVSNNDIGEAGARVLGQGLADSACQLETLRLENCGLTPANCKDLC
164    SMLRAKPDFKELIVSNNDINEAGVRVLCQGLKDSPCQLEALKLESCGVTSDNCRDLC

216    DVVASKASLQELDLGSNKLGNTGIAALCSGLLLPSCRLRTLWLWDCDVTAEGCKDLC
216    GIVASQASLRELDLGSNGLGDAGIAELCPGLLSPASRLKTLWLWECDITASGCRDLC
221    GIVASKASLRELALGSNKLGDVGMAELCPGLLHPSSRLRTLWIWECGITAKGCGDLC

273    RVLRAKQSLKELSLAGNELKDEGAQLLCESLLEPGCQLESLWVKTCSLTAASCPHFC
273    RVLQAKETLKELSLAGNKLGDEGARLLCESLLQPGCQLESLWVKSCSLTAACCQHVS
278    RVLRAKESLKELSLAGNELGDEGARLLCETLLEPGCQLESLWVKSCSFTAACCSHFS

330    SVLTKNSSLFELQMSSNPLGDSGVVELCKALGYPDTVLRVLWLGDCDVTDSGCSSLA
330    IMLTQNKHLLELQLSSNKLGDSGIQELCQALSQPGTTLRVLCLGDCEVTNSGCSSLA
335    SVLAQNRFLLELQISNNRLEDAGVRELCQGLGQPGSVLRVLWLADCDVSDSSCSSLA

387    TVLLANRSLRELDLSNNCMGDNGVLQLLESLKQPSCILQQLVLYDIYWTDEVEDQLR
387    SLLLANRSLRELDLSNNCVGDPGVLQLLGSLEQPGCALEQLVLYDTYWTEEVEDRLQ
394    ATLLANHSLRELDLSNNCLGDAGILQLVESVRQPGCLLEQLVLYDIYWSEEMEDRLQ

444 ALEEERPSLRILS    456    SEQ:ID NO:1
444 ALEGSKPGLRVLS    456    SEQ:ID NO:2
449 ALEKDKPSLRVLS    461    SEQ:ID NO:3
```

FIG 7

OXIDATION-RESISTANT RIBONUCLEASE INHIBITOR

STATEMENT REGARDING FEDERALLY SPONSORED RESEARCH OR DEVELOPMENT

The work described herein was supported in part by NIH Grants GM44783, CA73808 and AR44276, and NSF Grant BES9604563. The federal government may have certain rights in this invention.

CROSS-REFERENCE TO RELATED APPLICATIONS

Not applicable.

BACKGROUND OF THE INVENTION

In modern biotechnology, it is common practice to clone DNA sequences from biological organisms of any type and then to introduce genetic constructs carrying those sequences into plasmids or viral vectors for replication in vitro. Often these sequences are assembled into expression vectors which are then introduced into and expressed in foreign hosts of any of a number of organisms both eukaryotic and prokaryotic. In its isolated form, DNA can be studied, and its sequence can be determined. From a DNA sequence the structure and encoding capacity and other attributes of the DNA can be analyzed. It is also possible to synthesize altered and/or synthetic DNA sequences to make new gene products and to alter the genetic sequence of organisms both large and small.

In the process of expressing a coding sequence of DNA to make a protein, a first step involves the process of transcription whereby a messenger RNA sequence is made, which is ultimately translated into protein. Since the DNA and RNA are essential parts of the protein production process, it is undesirable during the process of in vitro cloning and expression of these nucleotides that the nucleotide chains be degraded. Nevertheless, since imperfectly purified biological reagents are conventionally used in such in vitro processes, the inadvertent introduction of unwanted enzymes is a very practical problem. All organisms make in their cells enzymes known as ribonucleases, which have the principal function of degrading nucleic acids in the cells. Such degradation is an essential part of biological processes both to down regulate messenger RNA which is no longer desired and also as a part of the cellular recycling process in which the component parts of nucleic acids are reused to synthesize other nucleic acids. Therefore, ribonucleases are ubiquitous in biological organisms. Ribonucleases also tend to be stable and highly active. Even trace amounts of ribonucleases can be lethal to in vitro DNA expression systems or systems for handling, utilizing or characterizing RNA, since even a trace amount of a ribonuclease can rapidly degrade all of the mRNA in an experimental sample.

Accordingly, companies which specialize in selling products to researchers in modern biotechnology supply reagents which are specifically intended to help overcome the problem of contaminating trace ribonucleases. Several companies sell, for example, ribonuclease-free water. There is a market for ribonuclease-free water because normal tap water can often be contaminated with extremely small amounts of ribonucleases, which can nevertheless severely disrupt experiments sensitive to such enzymatic activity. Experimenters hands contain ribonucleases which, through insufficiently careful lab techniques, can be introduced to and contaminate the results of carefully done in vitro experiments. Thus the avoidance of contamination by the action of ribonucleases is a significant consideration in many types of experiments in molecular biology.

Ribonucleases can be inhibited by protein molecules produced by cells, the specific purpose of which is to inhibit the enzymatic activity of a ribonuclease. Such proteins are called, naturally enough, ribonuclease inhibitors (or RI). The desirability of ribonuclease inhibitors for use in laboratory techniques of modern biotechnology has led to purified ribonuclease inhibitors being commercial products currently sold on the market by several reagent supply companies. Ribonuclease inhibitor can be isolated from many types of cells, notably most conveniently from placental cells, or it can be created by in vitro expression of DNA sequence which encodes ribonuclease inhibitor. U.S. Pat. No. 5,552,302 describes methods for the production of human recombinant placental ribonuclease inhibitor in prokaryotic cells.

It is a limitation on the ribonuclease inhibitors currently on the market place that they are not very stable, and certainly not as stable as the ribonucleases which they inhibit. Ribonuclease inhibitors tend to be susceptible to rapid oxidation. The oxidation of the ribonuclease inhibitor is a rapid cascading process which is irreversible. The ribonuclease inhibitor has to be completely reduced to bind to a ribonuclease. Since oxygen is, of course, prevalent in the environment, as are many oxidizing agents, this oxidation sensitivity is a severe limitation on the use of ribonuclease inhibitors that reduces their convenient use in laboratory practice of modern techniques of biotechnology. Accordingly, a ribonuclease inhibitor having less susceptibility to oxidation would be more advantageous, because it would be more stable and therefore more likely to decrease the loss of valuable nucleotides to the activity of unwanted ribonucleases.

BRIEF SUMMARY OF THE INVENTION

The present invention is summarized in a mutant ribonuclease inhibitor which has been modified so as to change cysteine residues from the native form of the ribonuclease inhibitor to other amino acids that will not form disulfide bonds. These changes to the amino acid sequence are directed to the location of adjacent cysteine residues in the sequence of ribonuclease inhibitor. Adjacent cysteine residues naturally occur in many, although not all, ribonuclease inhibitors.

It is an object of the present invention to provide a mutant form of a ribonuclease inhibitor that is less susceptible to oxidation and therefore more stable in its use in inhibiting the activity of ribonucleases in molecular biology procedures.

It is a feature of the present invention in that modifications of the sequence of ribonuclease inhibitors which include modifying cysteine residues where they are adjacent to each other results in mutant forms of ribonuclease inhibitor that still have appropriate specificity and binding affinity to ribonucleases but are more resistant to oxidation.

Other objects, advantages, and features of the present invention will become apparent from the following specification when taken in conjunction with the accompanying drawings.

BRIEF DESCRIPTION OF THE DRAWINGS

FIG. 7 illustrates the sequence comparisons among several ribonuclease inhibitors.

DETAILED DESCRIPTION OF THE INVENTION

The work described herein is based on a premise. The premise is that the observed instability of ribonuclease inhibitor molecules occurs because of oxidation of cysteine residues to form disulfide bridges. The thesis is further that such disulfide bridges are most likely to form when cysteine residues containing unpaired thiol groups are closely adjacent to each other. Therefore, in accordance with the method described herein, the amino acid sequence of a ribonuclease inhibitor molecule is re-designed so as to avoid having cysteine residues which are adjacent or closely adjacent in the engineered ribonuclease inhibitor. It has been found that by making this change to the amino acid sequence of ribonuclease inhibitor, and thus forming mutant ribonuclease inhibitors, those mutant ribonuclease inhibitors are more oxidation resistant and have a greater stability during handling than the wild-type ribonuclease inhibitor on which they are based. In this way, the use of ribonuclease inhibitors in biological processes becomes more practical, as the ribonuclease inhibitors become more stable and require less special treatment in order to remain active.

It is a notable feature of ribonuclease inhibitor molecules that they are typically rich in cysteine residues. The human ribonuclease inhibitor is a 50 kilodalton molecule composed of 460 amino acids, of which 32 are cysteine residues. All of the cysteine residues must remain reduced for the human ribonuclease inhibitor to bind to a ribonuclease.

Figure 1:
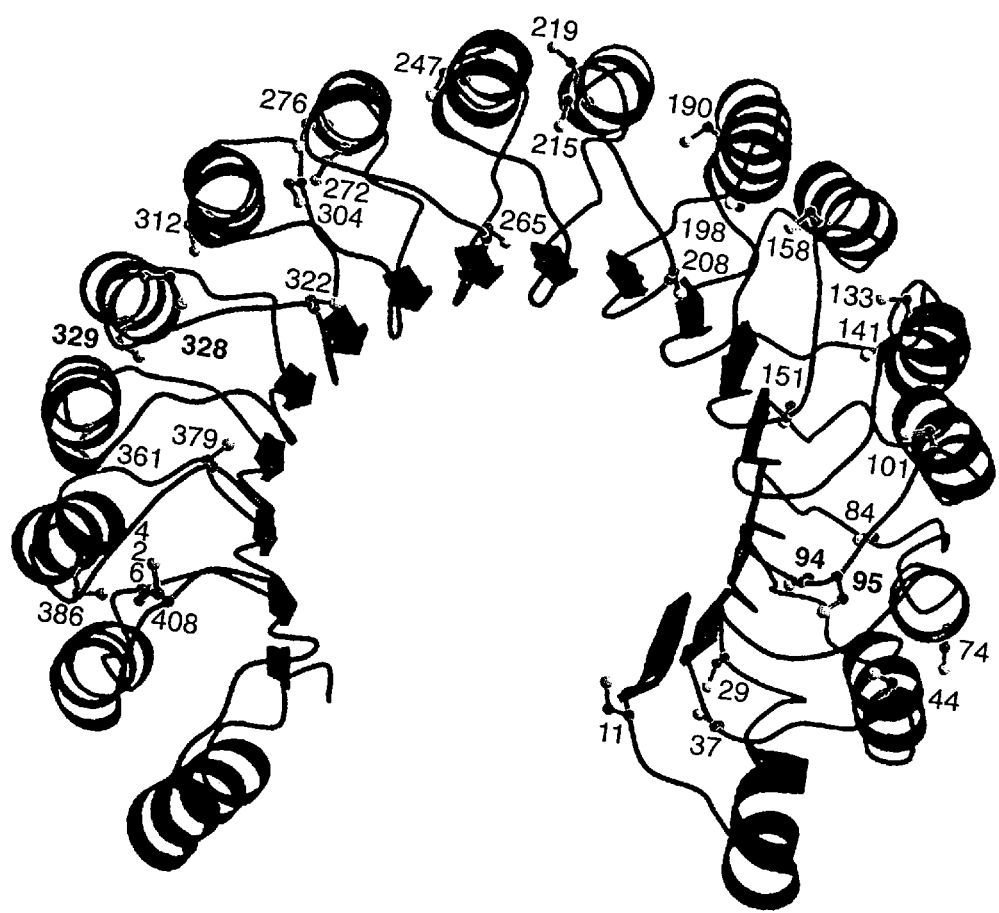
FIG. 1 is a graphical representation of the three dimensional structure of human ribonuclease inhibitor.

An illustration of the three dimensional structure of the human ribonuclease inhibitor is illustrated in FIG. 1. The sequence of the ribonuclease inhibitor can be found in Lee et al. *Biochemistry* 27:8545-8553 (1988), the disclosure of which is hereby incorporated by reference. From both FIG. 1 and the sequence of the protein, it can be readily seen that some of the cysteine residues are located adjacent to each other. The amino acid residues at positions numbered 94 and 95 and 328 and 329 in the human RI sequence as numbered in Lee et al., and as illustrated in FIG. 1, are all cysteines. It was theorized that these cysteine residues would be the most likely to be oxidized to form disulfide bonds which would interfere with the biological activity of the molecule. Note that in SEQ ID NO:3 below, these cysteine residues appear as amino acids 95, 96, 329 and 330, the difference being the N-terminal methionine which is counted as residue 1 in the deduced sequence of SEQ ID:NO:3 below and as residue 0 in the sequence of Lee et al.

Figure 2:
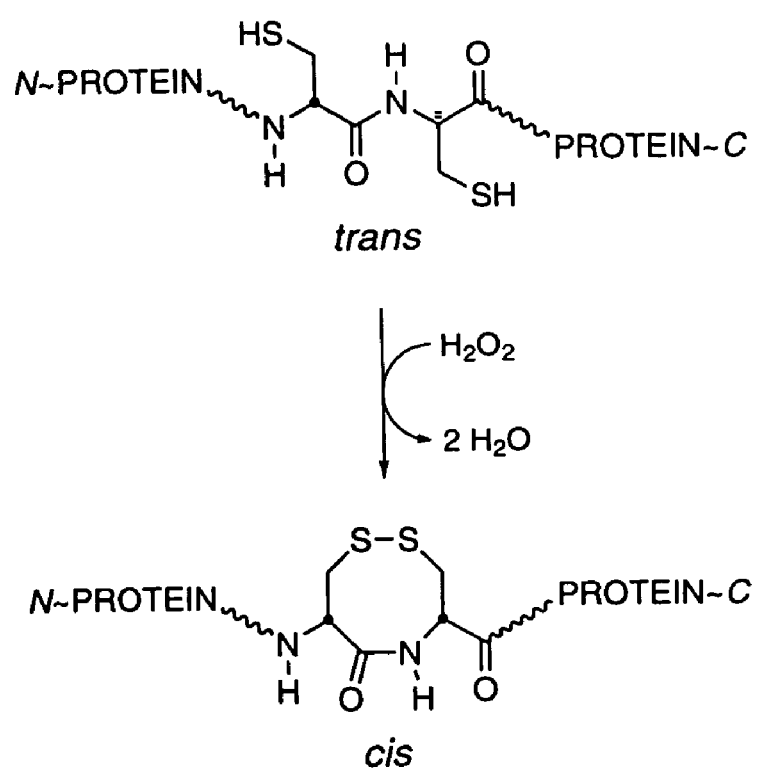
FIG. 2 illustrates the change in a peptide bond from a trans to a cis configuration.

When adjacent cysteine residues form a disulfide bond between them, the two cysteine residues together form an eight member ring that includes a polypeptide bond. Normally in a protein, a trans peptide bond is energetically favored over a cis peptide bond. A trans bond is, however, especially unstable in an eight-membered ring. It was demonstrated some time ago that trans-cyclooctene is much less stable than cis-cyclooctene, Turner and Meador *J. Am. Chem. Soc.* 79:4133-4136 (1957). This conformational energy analysis suggests that a peptide bond within a disulfide bond formed between adjacent cysteine residues will exist in the cis rather than the trans conformation. This is illustrated in FIG. 2. The strain in the cis peptide bond is overcome by the strength of the covalent disulfide bond. Indeed, oxidized cysteine residues with such cis peptide bonds have been found in crystalline methanol dehydrogenase and crystalline peptides. Blake, *Nature Struct. Biol.* 1:101-105; 557 (1994); Mez, *Crystl. Struct. Comm.*, 3:657-660 (1993). In solution, the peptide bond between two adjacent oxidized cysteine residues appear to be in conformational equilibrium, with either the trans conformation or the cis conformation predominating.

The formation of a disulfide bond between adjacent cysteine residues has structural consequences for the protein molecule in which they reside. In particular, a cis peptide bond is not tolerated in either an α-helix or β-sheet three-dimensional structure. Replacing a trans peptide bond with a cis peptide bond is therefore likely to distort the tertiary structure of a native protein. In human ribonuclease inhibitor, this distortion could bring together other pairs of cysteine residues, leading to further oxidation, and a cascade of transformational shape change. It was for this reason that it was decided to modify the coding sequence for the human ribonuclease inhibitor to remove adjacent cysteine residues, to prevent the formation of unwanted disulfide bonds between adjacent cysteine residues.

In native human ribonuclease inhibitor, the two pairs of cysteine residues which lie most adjacent to each other are the cysteines at amino acids 95 and 96 (which are in a loop) and the cysteines at amino acid 329 and 330 which reside in an α-helix. None of these four cysteine residues are in contact with angiogenin in the complex which forms between human ribonuclease inhibitor and angiogenin. Porcine ribonuclease inhibitor has one pair of adjacent cysteine residues, which are homologous to the cysteines at residues 329 and 330 in the human RI sequence. In contrast, ribonuclease inhibitor from rat has no pairs of adjacent cysteine residues. The oxidative stability of the rat ribonuclease inhibitor protein, as well as its three-dimensional structure, is currently not known.

As will be discussed with the experimental results below, it was found possible to inhibit the formation of disulfide bonds between adjacent cysteine residues of a ribonuclease inhibitor by replacing the adjacent cysteine residues with alanine residues. The mutant human pancreatic ribonuclease inhibitor molecules thus created, have pairs of alanine-for-cysteine substitutions at both amino acids 95 and 96, at both amino acid positions 329 and 330, or substitutions for all four of the cysteine residues. It was demonstrated that the replacing of any or all of the cysteine residues with alanine did not markedly impair the ability of the human ribonuclease inhibitor to bind RNase A. There was, however, some slight diminution in affinity to ribonuclease for some of the variants.

It was discovered, however, that replacing these adjacent cysteine residues with alanine residues made the human ribonuclease inhibitor significantly more oxidation resistant as compared to the wild-type protein. Oxidation resistance was tested using hydrogen peroxide based on ease of laboratory use. It was discovered that the wild-type human ribonuclease inhibitor loses 50% of its activity in a solution which has little as 0.007% hydrogen peroxide volume-per-volume. By contrast, the mutant ribonuclease inhibitor having alanine substitutions at amino acid positions 329 and 330 retain 50% of its ribonuclease inhibitor activity at 0.09% volume-per-volume hydrogen peroxide. By this measure, the mutant C329/C330A ribonuclease inhibitor variant is 10 to 15 fold more resistant to oxidative damage than is the wild-type human ribonuclease inhibitor.

In this way, it is possible to create mutants of wild-type human ribonuclease inhibitor which are more oxidation resistant than the wild types. Such oxidation resistance is created by the substitution of another amino acid for at least one of the adjacent cysteine residues within the molecule. Such oxidation resistant variants of ribonuclease inhibitor are useful for a wide variety of laboratory protocols which now would avoid the need for reducing agents in reactions containing ribonuclease inhibitor. The mutant variants of human ribonuclease inhibitor could serve another purpose. In addition to binding to ribonucleases, the ribonuclease inhibitor also binds to angiogenin. Angiogenin promotes neovascularization which is the formation of new blood vessels, and human ribonuclease inhibitor has been shown effective in inhibiting angiogenin mediated vascularization. In such physiological experiments, human ribonuclease inhibitor is exposed to an oxidative environment, and it is known that such an environment can compromise its ability to inhibit angeniogenin. It is therefore likely that the oxidation resistant variants of ribonuclease inhibitor as described herein would be more effective than wild-type human ribonuclease inhibitor at inhibiting angiogenin mediated angiogenesis. That prospect has both clinical and diagnostic implications.

The methodology disclosed here will be equally effective for ribonuclease inhibitor molecules from other species. Shown in FIG. 7 is a comparison of the amino acid sequences of RNASE inhibitor from rat, pig, and human. Note that pig RI shares the adjacent cysteine residues (at positions 323 and 324) corresponding to residues 329 and 330 of the human sequence, and thus could be modified as described here. The technique described here will work with all such RI molecules that natively have adjacent cysteine residues. Some RI variants, like the rat molecule illustrated in FIG. 7, contain no adjacent cysteines.

EXAMPLES

The goal of the work described below was to create mutant forms of human ribonuclease inhibitor which would hinder the cataclysmic oxidation of human ribonuclease inhibitor. Reasoning that the formation of disulfide bonds amongst cysteine residues in the human ribonuclease inhibitor molecule would be most likely to occur among those residues which were closest in space, it was decided to survey the three-dimensional structure of ribonuclease inhibitor to determine those residues which were closest to each other in the normal three-dimensional conformational structure of human ribonuclease inhibitor. FIG. 1 is an illustration of the 3D model that was used for the structure of human ribonuclease inhibitor. Study of that structure revealed that the most proximal cysteine residues in native human ribonuclease inhibitor are those which are adjacent in the primary amino acid sequence as published by Lee et al. (*Biochemistry* 27:8545-8553 (1988)). The close amino acid residues were the cysteines at amino acid positions 95 and 96, which are in a loop structure, and the cysteines at residues 329 and 330, which are part of an alpha helix structure. None of these four cysteine residues contacts angiogenin during the formation of the ribonuclease inhibitor complex with angiogenin. It was observed that porcine ribonuclease inhibitor varies from the human sequence in that it has only one pair of adjacent cysteine residues, which are homologous to cysteines 329 and 330 in the human ribonuclease inhibitor complex. By contrast, rat ribonuclease inhibitor has no pairs of adjacent cysteine residues, but the oxidative stability of the rat protein, as well as its three-dimensional structure, is currently unknown.

When adjacent cysteine residues form a disulfide bond, the resulting cysteine residues define an eight-membered ring that includes a peptide bond. Normally in a protein a trans (i.e.

Z) peptide bond is more favored energetically as compared to a cis (i.e. E) peptide bond. A trans bond is, however, especially unstable in an eight-membered ring. These conformational energetics suggest that a peptide bond within a disulfide bond formed between adjacent cysteine residues would tend to be in the cis, rather than the trans, conformation. This is illustrated in FIG. 2.

The strain of the cis peptide bond is overcome by the strength of the covalent disulfide bond which has a disassociation energy equal to 65 kcal/mol in $H_3CS$—$SCH_3$. Indeed such cysteine residues with cis peptide bonds have been found in crystalline methanol dehydrogenase and crystalline peptides. Further, the stability of an intramolecular disulfide bond in the generalized structure Cys-(Ala)$_n$-Cys peptides is greater for n=0 than for n=2, 4, or 5 (Zhang and Schneider, *J. Bio. Chem.* 264:18472-18479 (1989)). In solution, the peptide bond within adjacent disulfide-bonded cysteine residues appears to be in conformational equilibrium with either the trans conformation or the cis confirmation predominating.

The formation of a disulfide bond between adjacent cysteine residues has structural implications for the overall protein molecule of which it is a part. In particular, a cis peptide bond is inconsistent with an α-helix or a β-sheet secondary structure. Replacing a trans peptide bond with a cis peptide bond distorts the structure of the native protein. In human ribonuclease inhibitor, distortion could congregate other pairs of cysteine residues leading to further oxidation and potentially catastrophic degradation of the biologically active form in the molecule.

RNASE A for use in this work was produced in *Escherichia coli* with a recombinant DNA expression system, as described in delCardayre et al., *Protein Engng.* 8:261-273 (1995). Wild-type hRI and its variants were produced in *E. coli* by using plasmid pET-RI, which directs the expression of hRI as described in Leland et al., *Proc. Natl. Acad. Sci. USA* 95:10407-10412 (1998). To produce hRI variants, the cDNA that codes for hRI was mutated by the method of Kunkel et al. *Methods Enzymol.* 154:367-382 (1987). The oligonucleotides used were BMK14 (C95A/C96A; HindIII):GGC-CCCCGTCAGCGCCGCGTTCTGGAG-GCTAAGCTTCTG (SEQ ID NO:4); BMK16 (C329A/C330A; NheI): GCTGAAGTGGCTAGCGGCGGCGGCTGTGAA (SEQ ID NO:5); BMK17(C329A; SphI):GCTGAAGTGGGAG-CATGCGGCGGCTGTGAA (SEQ ID NO:6); and BMK18 (C330A; NheI):GCTGAAGTGGCTAGCGCAGGCGGCT-GTGAA (SEQ ID NO:7). In these sequences, the reverse complement of new alanine codons is in bold type and new restriction endonuclease sites are underlined. cDNA sequences of mutated plasmids were determined with an ABI 373 Automated Sequencer.

Wild-type hRI and the variants were produced and purified essentially as described (Leland et al., supra). The key step in the purification protocol is affinity chromatography on RNASE A-Sepharose 4B resin. Briefly, *E. coli* lysate in 50 mM potassium phosphate buffer, pH 7.5, containing glycerol (15% v/v), DTT (5 mM), and EDTA (1 mM) was loaded onto the resin. Only active molecules of hRI are bound by the immobilized RNASE A. The loaded resin was washed with 50 mM potassium phosphate buffer, pH 7.5, containing NaCl (0.5 M) and DTT (8 mM), and eluted with 0.10 M sodium acetate buffer, pH 5.0, containing glycerol (15% v/v), NaCl (3.0 M), and DTT (8 mM).

The presence of 8 mM DTT would interfere in assays of oxidation resistance. To prepare hRI for the assays described below, the concentration of DTT was reduced by $10^3$-fold by concentration/dilution. Briefly, hRI was concentrated 10-fold by ultrafiltration using a Microcon 10 micron concentrator from Amicon (Beverly, Mass.). The resulting solution was diluted 10-fold with degassed 20 mM HEPES-HCl buffer, pH 7.6, containing glycerol (50% v/v) and KCl (50 mM). This treatment was repeated three times. hRI thus treated retains full activity, provided that its exposure to air is minimal.

Concentrations of RNASE A were determined by assuming that A=0.72 at 277.5 nm for a 1.00 mg/mL solution. Concentrations of hRI were determined by assuming that A=0.88 at 280 nm for a 1.00 mg/mL solution as described in Ferreras et al., *J. Biol. Chem.* 270:28570-28578 (1995). Concentrations of poly(cytidylic acid)[poly(C)] were determined by assuming that $\epsilon=6200$ $M^{-1}cm^{-1}$ per nucleotide at 268 nm as per Yakovlev et al., *Eur. J. Biochem.* 204:187-190 (1992).

To assay for inhibition of RNASE A, serial dilutions were made to produce six solutions (10 μL each) of 20 mM HEPES-HCl buffer, pH 7.6, containing KCl (50 MM) and hRI (10 nM-10 μM). A solution (101) of 20 mM HEPES-HCl buffer, pH 7.6, containing KCl (50 mM) and RNASE A (80 nM) was added to each of the hRI solutions. The resulting mixtures were incubated at 37° C. for 5 min. The ribonucleolytic activity in each mixture was then assessed by using a spectrophotometric assay for poly(C) cleavage, as described (delCardayre et al., 1995), with [poly(C)]=37 μM. This experiment was performed at least twice with wild-type hRI and each variant.

To test for oxidation resistance, serial dilutions were made to produce seven solutions (5 μL each) of 20 mM HEPES-HCl buffer, pH 7.6, containing KCl (50 mM) and $H_2O_2$ (0.004-2% v/v, which is 2 mM-0.9M). A solution (5 μl) of 20 mM HEPES-HCl buffer, pH 7.6, containing KCl (50 mM) and hRI (10 μM) was added to each of the $H_2O_2$ solutions. The resulting mixtures were incubated at 37° C. for 30 min. A solution (10 μL) of 20 mM HEPES-HCl buffer, pH 7.6, containing KCl (50 mM) and RNASE A (80 nM) was then added to each $H_2O_2$ plus hRI solution. The resulting mixtures were incubated at 37° C. for 5 min. The ribonucleolytic activity in each mixture was then assessed by using a spectrophotometric assay for poly(C) cleavage as described (delcardayre et la., 1995), with [poly(C)]=37 μM. This experiment was performed at least twice with wild-type hRI and each variant.

Figures 3, 4:
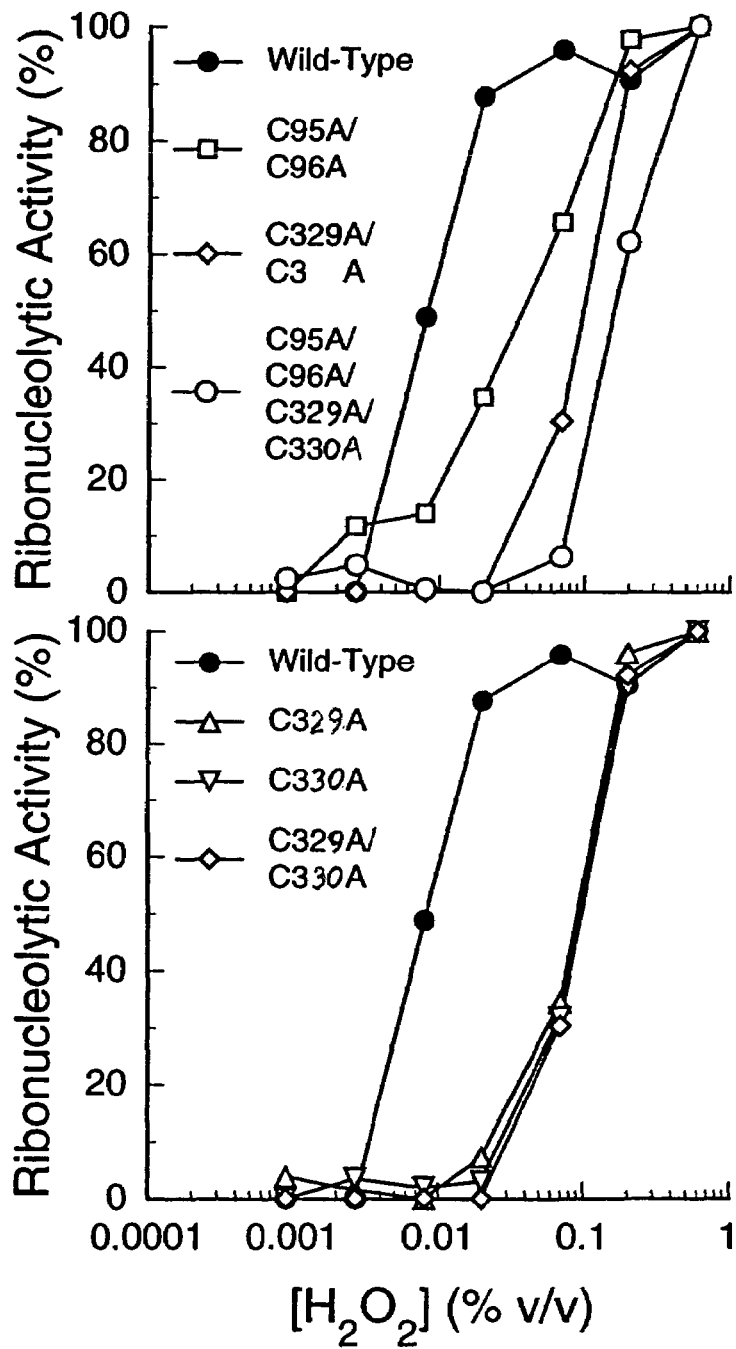
FIG. 3 is a graphical illustration of some of the results of tests conducted as described in the examples below.
FIG. 4 is a graphical illustration of additional experimental results.

It has been previously reported that the cysteines at residues 95, 96, 329, and 330 of hRI do not contact angiogenin in the complex formed between human ribonuclease inhibitor and angiogenin. Thus it was not anticipated that replacing any of these cysteine residues with alanine would significantly impair the ability of human ribonuclease inhibitor to bind to ribonuclease A. Shown in FIGS. 3 and 4 is a graphical representation of the data showing the ability of the various modified or mutant human ribonuclease inhibitors to inhibit ribonucleolytic activity. These results demonstrate that none of the substitutions significantly impair the ability of the mutant forms of human ribonuclease inhibitor to bind to ribonuclease A. However, C95A/C96A hRI (human ribonuclease inhibitor with cysteines at 95 and 96 substitute by alanine) and C95A/C96A/C329A/C330A hRI are slightly less effective inhibitors of ribonuclease activity than is the variant C329A/C330A The affinity of the two single amino acid mutations variants, C329A hRI and C330A hRI for human ribonuclease inhibitor is between that of the wild-type human ribonuclease inhibitor and the C329A/C330A variant as shown in FIG. 4.

Figure 5:
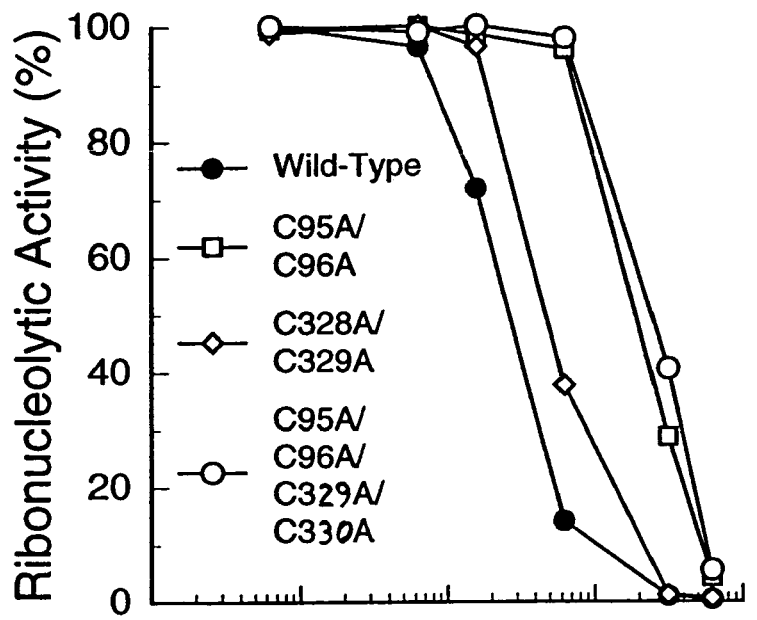
FIG. 5 is a graphical illustration of yet additional experimental results.

The test for oxidation resistance demonstrated that replacing adjacent cysteine residues with alanine makes the resulting mutant hRI oxidation resistant. As the oxidant in this test we chose $H_2O_2$, which is easier to dispense than $O_2$ gas and which likewise oxidizes thiols to disulfides. As shown in FIG. 5, $H_2O_2$ has a greater effect on C329A/C330A human ribonuclease inhibitor than it has on the C95A/C96A variant. In our assays, wild-type human ribonuclease inhibitor loses 50% of its activity at 0.007% volume per volume $H_2O_2$. By contrast, C329A/C330A mutant human ribonuclease inhibitor retains 50% of its activity at 0.09% volume per volume $H_2O_2$. By this measure, the C329A/C330A mutant form of ribonuclease inhibitor is ten to fifteen times more resistant to oxidative damage than is the wild-type human ribonuclease inhibitor.

Figure 6:
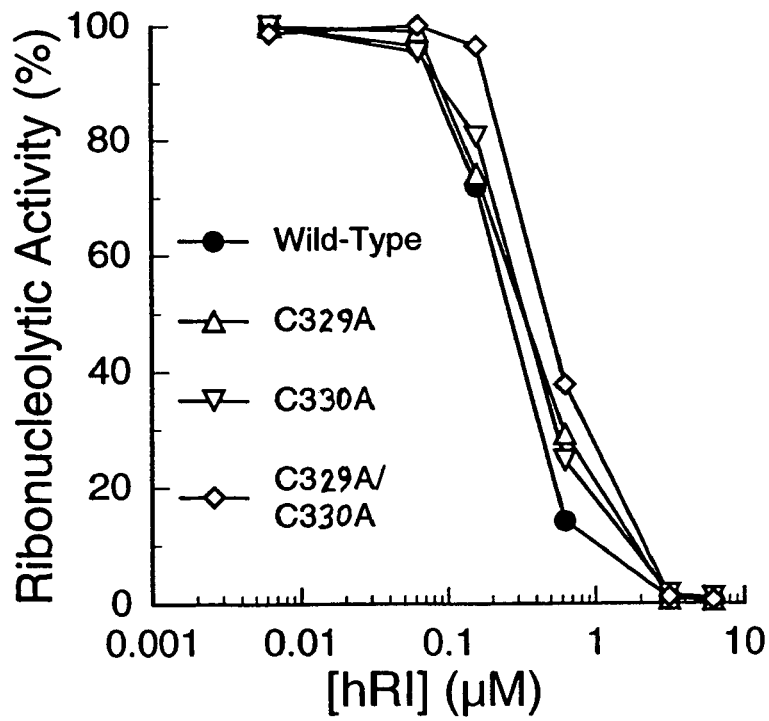
FIG. 6 is another graphical illustration of results from the examples below.

The enhanced oxidation resistance of C329A/C330A mutant hRI appears to result from the inhibition of the formation of a disulfide bond between the cysteines which would otherwise reside at residues 329 and 330. As shown in FIG. 6, the individual C329A and C330A variants of mutant variants of hRI are just as resistant to oxidation by $H_2O_2$ as is the C329A/C330A form of hRI. The simplest explanation for this result is that oxidation of the wild-type protein results in a Cys-329-Cys-330 disulfide bond which cannot form in either of the single amino acid variants C329A or C330A, or in the double amino acid variant C329A/C330A.

High levels of $H_2O_2$ (such as the 0.09% volume per volume, which equals 0.04M) inactivate all five forms of mutant human ribonuclease inhibitor. At least two explanations are possible for this result. Disulfide bonds can form between thiols of nonadjacent cysteine residues. Alternatively, thiols of hRI that contact RNASE A in the hRI complex with RNASE A could be oxidized to form sulfonates ($RSO_3^-$). Such over-oxidation is more likely with $H_2O_2$ than with diatomic oxygen gas.

Currently commercial human ribonuclease inhibitor is distributed in solutions containing millimolar levels of dithiothreitol (DTT). The presence of this reducing agent is included with the ribonuclease inhibitor to maintain the hRI in a reduced, and hence active, form. In many instances, such reducing agents are incompatible with laboratory protocols. Moreover, reducing agents are oxidized and thus rendered ineffective by the ubiquitous oxidant oxygen gas and transition metal ions. We find that replacing only one (i.e. Cys 329 or Cys 330) of the 32 cysteine residues in hRI with an alanine residue substantially increases the resistance of the molecule to oxidation, without compromising its affinity for RNAase A. This demonstrates that variants of hRI lacking a cysteine residue at positions 329 or 330, or the homologous positions in other ribonuclease inhibitors, will be more useful than wild-type ribonuclease inhibitors in many laboratory protocols.

Oxidation resistant variants of ribonuclease inhibitor can serve another purpose. Angiogenin, like ribonuclease A, is tightly bound by ribonuclease inhibitor. As its name implies, angiogenin promotes neovascularization or the formation of new blood vessels. Ribonuclease inhibitor has been shown to be effective in inhibiting angiogenin-mediated neovascularization. In psychological experiments ribonuclease inhibitor is exposed to an oxidative environment, which could compromise its ability to inhibit angiogenin. This phenomenon would indicate that oxidation resistant variants, such as those described herein, would be more effective than wild-type ribonuclease inhibitor at inhibiting angiogenin-mediated angiogenesis.

I claim:

1. An oxidation-resistant engineered ribonuclease inhibitor (RI) selected from the group consisting of:
   (i) a RI comprising the reference sequence of SEQ ID NO: 3, except for an alanine substitution of at least one cysteine residue at positions 95, 96, 329 and 330; and
   (ii) a RI comprising the reference sequence of SEQ ID NO: 2, except for an alanine substitution of at least one cysteine residue at positions 324 and 325,
   the RI having a greater resistance to oxidation relative to the reference sequence for the RI and retaining its specificity and binding affinity to ribonuclease.

2. The RI of claim 1, wherein the alanine substitution inhibits the formation of a disulfide bond with an adjacent cysteine residue.

3. The RI of claim 1, wherein the RI is 10 to 15 fold more resistant to oxidative damage than a RI comprising the relevant reference sequence.

4. The RI of claim 1, wherein the RI exhibits an in vitro inhibition of ribonucleolytic activity.

5. An oxidation-resistant ribonuclease inhibitor (RI) comprising the reference sequence of SEQ ID NO: 3, except for an alanine residue at one or more of positions 95, 96, 329 and 330.

6. The RI of claim 5, wherein the RI retains specificity and affinity of SEQ ID NO:3 for binding to angiogenin.

7. The RI of claim 5, wherein the residues at positions 329 and 330 are alanine residues.

8. An oxidation-resistant ribonuclease inhibitor (RI) comprising the reference sequence of SEQ ID NO: 2, except for an alanine residue at one or both of positions 324 and 325.

9. The RI of claim 8, wherein the residues at positions 324 and 325 are alanine residues.

10. The RI of claim 5, wherein the residues at positions 95 and 96 are alanine residues.

11. The RI of claim 5, wherein the residues at positions 95, 96, 329 and 330 are alanine residues.

* * * * *

SEQUENCE LISTING

<160> NUMBER OF SEQ ID NOS: 7

<210> SEQ ID NO 1
<211> LENGTH: 456
<212> TYPE: PRT
<213> ORGANISM: Rattus sp.

<400> SEQUENCE: 1

```
Met Ser Leu Asp Ile Gln Cys Glu Gln Leu Ser Asp Ala Arg Trp Thr
 1               5                  10                  15

Glu Leu Leu Pro Leu Ile Gln Gln Tyr Gln Val Val Arg Leu Asp Asp
             20                  25                  30

Cys Gly Leu Thr Glu Val Arg Cys Lys Asp Ile Arg Ser Ala Ile Gln
         35                  40                  45

Ala Asn Pro Ala Leu Thr Glu Leu Ser Leu Arg Thr Asn Glu Leu Gly
     50                  55                  60

Asp Ala Gly Val Gly Leu Val Leu Gln Gly Leu Gln Asn Pro Thr Cys
 65                  70                  75                  80

Lys Ile Gln Lys Leu Ser Leu Gln Asn Cys Ser Leu Thr Glu Ala Gly
                 85                  90                  95

Cys Gly Val Leu Pro Asp Val Leu Arg Ser Leu Ser Thr Leu Arg Glu
            100                 105                 110

Leu His Leu Asn Asp Asn Pro Leu Gly Asp Glu Gly Leu Lys Leu Leu
        115                 120                 125

Cys Glu Gly Leu Arg Asp Pro Gln Cys Arg Leu Glu Lys Leu Gln Leu
    130                 135                 140

Glu Tyr Cys Asn Leu Thr Ala Thr Ser Cys Glu Pro Leu Ala Ser Val
145                 150                 155                 160

Leu Arg Val Lys Pro Asp Phe Lys Glu Leu Val Leu Ser Asn Asn Asp
                165                 170                 175

Phe His Glu Ala Gly Ile His Thr Leu Cys Gln Gly Leu Lys Asp Ser
            180                 185                 190

Ala Cys Gln Leu Glu Ser Leu Lys Leu Glu Asn Cys Gly Ile Thr Ser
        195                 200                 205

Ala Asn Cys Lys Asp Leu Cys Asp Val Val Ala Ser Lys Ala Ser Leu
    210                 215                 220

Gln Glu Leu Asp Leu Gly Ser Asn Lys Leu Gly Asn Thr Gly Ile Ala
225                 230                 235                 240

Ala Leu Cys Ser Gly Leu Leu Leu Pro Ser Cys Arg Leu Arg Thr Leu
                245                 250                 255

Trp Leu Trp Asp Cys Asp Val Thr Ala Glu Gly Cys Lys Asp Leu Cys
            260                 265                 270

Arg Val Leu Arg Ala Lys Gln Ser Leu Lys Glu Leu Ser Leu Ala Gly
        275                 280                 285

Asn Glu Leu Lys Asp Glu Gly Ala Gln Leu Leu Cys Glu Ser Leu Leu
    290                 295                 300

Glu Pro Gly Cys Gln Leu Glu Ser Leu Trp Val Lys Thr Cys Ser Leu
305                 310                 315                 320

Thr Ala Ala Ser Cys Pro His Phe Cys Ser Val Leu Thr Lys Asn Ser
                325                 330                 335

Ser Leu Phe Glu Leu Gln Met Ser Ser Asn Pro Leu Gly Asp Ser Gly
            340                 345                 350

Val Val Glu Leu Cys Lys Ala Leu Gly Tyr Pro Asp Thr Val Leu Arg
```

-continued

```
                355                 360                 365
Val Leu Trp Leu Gly Asp Cys Asp Val Thr Asp Ser Gly Cys Ser Ser
370                 375                 380

Leu Ala Thr Val Leu Leu Ala Asn Arg Ser Leu Arg Glu Leu Asp Leu
385                 390                 395                 400

Ser Asn Asn Cys Met Gly Asp Asn Gly Val Leu Gln Leu Leu Glu Ser
                405                 410                 415

Leu Lys Gln Pro Ser Cys Ile Leu Gln Gln Leu Val Leu Tyr Asp Ile
                420                 425                 430

Tyr Trp Thr Asp Glu Val Glu Asp Gln Leu Arg Ala Leu Glu Glu Glu
                435                 440                 445

Arg Pro Ser Leu Arg Ile Ile Ser
                450                 455

<210> SEQ ID NO 2
<211> LENGTH: 456
<212> TYPE: PRT
<213> ORGANISM: Sus sp.

<400> SEQUENCE: 2

Met Asn Leu Asp Ile His Cys Glu Gln Leu Ser Asp Ala Arg Trp Thr
  1               5                  10                  15

Glu Leu Leu Pro Leu Leu Gln Gln Tyr Glu Val Val Arg Leu Asp Asp
                 20                  25                  30

Cys Gly Leu Thr Glu Glu His Cys Lys Asp Ile Gly Ser Ala Leu Arg
             35                  40                  45

Ala Asn Pro Ser Leu Thr Glu Leu Cys Leu Arg Thr Asn Glu Leu Gly
         50                  55                  60

Asp Ala Gly Val His Leu Val Leu Gln Gly Leu Gln Ser Pro Thr Cys
 65                  70                  75                  80

Lys Ile Gln Lys Leu Ser Leu Gln Asn Cys Ser Leu Thr Glu Ala Gly
                 85                  90                  95

Cys Gly Val Leu Pro Ser Thr Leu Arg Ser Leu Pro Thr Leu Arg Glu
            100                 105                 110

Leu His Leu Ser Asp Asn Pro Leu Gly Asp Ala Gly Leu Arg Leu Leu
        115                 120                 125

Cys Glu Gly Leu Leu Asp Pro Gln Cys His Leu Glu Lys Leu Gln Leu
130                 135                 140

Glu Tyr Cys Arg Leu Thr Ala Ala Ser Cys Glu Pro Leu Ala Ser Val
145                 150                 155                 160

Leu Arg Ala Thr Arg Ala Leu Lys Glu Leu Thr Val Ser Asn Asn Asp
                165                 170                 175

Ile Gly Glu Ala Gly Ala Arg Val Leu Gly Gln Gly Leu Ala Asp Ser
            180                 185                 190

Ala Cys Gln Leu Glu Thr Leu Arg Leu Glu Asn Cys Gly Leu Thr Pro
        195                 200                 205

Ala Asn Cys Lys Asp Leu Cys Gly Ile Val Ala Ser Gln Ala Ser Leu
    210                 215                 220

Arg Glu Leu Asp Leu Gly Ser Asn Gly Leu Gly Asp Ala Gly Ile Ala
225                 230                 235                 240

Glu Leu Cys Pro Gly Leu Leu Ser Pro Ala Ser Arg Leu Lys Thr Leu
                245                 250                 255

Trp Leu Trp Glu Cys Asp Ile Thr Ala Ser Gly Cys Arg Asp Leu Cys
            260                 265                 270
```

```
Arg Val Leu Gln Ala Lys Glu Thr Leu Lys Glu Leu Ser Leu Ala Gly
        275                 280                 285

Asn Lys Leu Gly Asp Glu Gly Ala Arg Leu Leu Cys Glu Ser Leu Leu
        290                 295                 300

Gln Pro Gly Cys Gln Leu Glu Ser Leu Trp Val Lys Ser Cys Ser Leu
305                 310                 315                 320

Thr Ala Ala Cys Cys Gln His Val Ser Leu Met Leu Thr Gln Asn Lys
                325                 330                 335

His Leu Leu Glu Leu Gln Leu Ser Ser Asn Lys Leu Gly Asp Ser Gly
        340                 345                 350

Ile Gln Glu Leu Cys Gln Ala Leu Ser Gln Pro Gly Thr Thr Leu Arg
        355                 360                 365

Val Leu Cys Leu Gly Asp Cys Glu Val Thr Asn Ser Gly Cys Ser Ser
        370                 375                 380

Leu Ala Ser Leu Leu Ala Asn Arg Ser Leu Arg Glu Leu Asp Leu
385                 390                 395                 400

Ser Asn Asn Cys Val Gly Asp Pro Gly Val Leu Gln Leu Leu Gly Ser
                405                 410                 415

Leu Glu Gln Pro Gly Cys Ala Leu Glu Gln Leu Val Leu Tyr Asp Thr
        420                 425                 430

Tyr Trp Thr Glu Glu Val Glu Asp Arg Leu Gln Ala Leu Glu Gly Ser
        435                 440                 445

Lys Pro Gly Leu Arg Val Ile Ser
        450                 455

<210> SEQ ID NO 3
<211> LENGTH: 461
<212> TYPE: PRT
<213> ORGANISM: Homo sapiens

<400> SEQUENCE: 3

Met Ser Leu Asp Ile Gln Ser Leu Asp Ile Gln Cys Glu Glu Leu Ser
 1               5                  10                  15

Asp Ala Arg Trp Ala Glu Leu Leu Pro Leu Leu Gln Gln Cys Gln Val
                20                  25                  30

Val Arg Leu Asp Asp Cys Gly Leu Thr Glu Ala Arg Cys Lys Asp Ile
            35                  40                  45

Ser Ser Ala Leu Arg Val Asn Pro Ala Leu Ala Glu Leu Asn Leu Arg
        50                  55                  60

Ser Asn Glu Leu Gly Asp Val Gly Val His Cys Val Leu Gln Gly Leu
65                  70                  75                  80

Gln Thr Pro Ser Cys Lys Ile Gln Lys Leu Ser Leu Gln Asn Cys Cys
                85                  90                  95

Leu Thr Gly Ala Gly Cys Gly Val Leu Ser Ser Thr Leu Arg Thr Leu
                100                 105                 110

Pro Thr Leu Gln Glu Leu His Leu Ser Asp Asn Leu Leu Gly Asp Ala
        115                 120                 125

Gly Leu Gln Leu Leu Cys Glu Gly Leu Leu Asp Pro Gln Cys Arg Leu
        130                 135                 140

Glu Lys Leu Gln Leu Glu Tyr Cys Ser Leu Ser Ala Ala Ser Cys Glu
145                 150                 155                 160

Pro Leu Ala Ser Val Leu Arg Ala Lys Pro Asp Phe Lys Glu Leu Thr
                165                 170                 175

Val Ser Asn Asn Asp Ile Asn Glu Ala Gly Val Arg Val Leu Cys Gln
                180                 185                 190
```

```
Gly Leu Lys Asp Ser Pro Cys Gln Leu Glu Ala Leu Lys Leu Glu Ser
            195                 200                 205

Cys Gly Val Thr Ser Asp Asn Cys Arg Asp Leu Cys Gly Ile Val Ala
        210                 215                 220

Ser Lys Ala Ser Leu Arg Glu Leu Ala Leu Gly Ser Asn Lys Leu Gly
225                 230                 235                 240

Asp Val Gly Met Ala Glu Leu Cys Pro Gly Leu Leu His Pro Ser Ser
                245                 250                 255

Arg Leu Arg Thr Leu Trp Ile Trp Glu Cys Gly Ile Thr Ala Lys Gly
            260                 265                 270

Cys Gly Asp Leu Cys Arg Val Leu Arg Ala Lys Glu Ser Leu Lys Glu
        275                 280                 285

Leu Ser Leu Ala Gly Asn Glu Leu Gly Asp Glu Gly Ala Arg Leu Leu
    290                 295                 300

Cys Glu Thr Leu Leu Glu Pro Gly Cys Gln Leu Glu Ser Leu Trp Val
305                 310                 315                 320

Lys Ser Cys Ser Phe Thr Ala Ala Cys Cys Ser His Phe Ser Ser Val
                325                 330                 335

Leu Ala Gln Asn Arg Phe Leu Leu Glu Leu Gln Ile Ser Asn Asn Arg
            340                 345                 350

Leu Glu Asp Ala Gly Val Arg Glu Leu Cys Gln Gly Leu Gly Gln Pro
        355                 360                 365

Gly Ser Val Leu Arg Val Leu Trp Leu Ala Asp Cys Asp Val Ser Asp
    370                 375                 380

Ser Ser Cys Ser Ser Leu Ala Ala Thr Leu Leu Ala Asn His Ser Leu
385                 390                 395                 400

Arg Glu Leu Asp Leu Ser Asn Asn Cys Leu Gly Asp Ala Gly Ile Leu
                405                 410                 415

Gln Leu Val Glu Ser Val Arg Gln Pro Gly Cys Leu Leu Glu Gln Leu
            420                 425                 430

Val Leu Tyr Asp Ile Tyr Trp Ser Glu Glu Met Glu Asp Arg Leu Gln
        435                 440                 445

Ala Leu Glu Lys Asp Lys Pro Ser Leu Arg Val Ile Ser
    450                 455                 460

<210> SEQ ID NO 4
<211> LENGTH: 39
<212> TYPE: DNA
<213> ORGANISM: Artificial Sequence
<220> FEATURE:
<223> OTHER INFORMATION: Description of Artificial Sequence: mutation
      sequence

<400> SEQUENCE: 4
ggcccccgtc agcgccgcgt tctggaggct aagcttctg                            39

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: mutation
      sequence

<400> SEQUENCE: 5
gctgaagtgg ctagcggcgg cggctgtgaa                                      30
```

-continued

```
<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: mutation
      sequence

<400> SEQUENCE: 6
gctgaagtgg gagcatgcgg cggctgtgaa                                            30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: mutation
      sequence

<400> SEQUENCE: 7
gctgaagtgg ctagcgcagg cggctgtgaa                                            30
```